United States Patent [19]
Fosker et al.

[11] 3,987,178
[45] Oct. 19, 1976

[54] α-AMINOCYCLOALKYLACETAMIDO PENICILLANIC ACIDS AND THEIR SALTS AND ESTERS

[75] Inventors: George Robert Fosker, Horsham; John Barry Harbridge, Coulsdon; Ronald Hubbard, Dorking, all of England

[73] Assignee: Beecham Group Limited, United Kingdom

[22] Filed: Dec. 15, 1972

[21] Appl. No.: 315,453

[30] Foreign Application Priority Data
Jan. 20, 1972 United Kingdom................. 2731/72

[52] U.S. Cl............................. 424/271; 260/239.1
[51] Int. Cl.² ....................................... C07D 499/66
[58] Field of Search................... 260/239.1; 424/271

[56] References Cited
UNITED STATES PATENTS

| | | | |
|---|---|---|---|
| 3,194,802 | 7/1965 | Alburn et al..................... | 260/239.1 |
| 3,471,475 | 10/1969 | Clark et al........................ | 260/239.1 |
| 3,494,915 | 2/1970 | Alburn et al..................... | 260/239.1 |
| 3,532,744 | 10/1970 | Fletcher et al................... | 260/239.1 |
| 3,553,201 | 10/1967 | Clark et al. ..................... | 260/239.1 |
| 3,573,279 | 3/1971 | Alburn et al..................... | 260/239.1 |
| 3,594,366 | 7/1971 | Grant et al....................... | 260/239.1 |
| 3,699,096 | 10/1972 | Weissenburger................. | 260/239.1 |

*Primary Examiner*—Nicholas S. Rizzo
*Assistant Examiner*—David E. Wheeler

[57] ABSTRACT

A class of amino alicyclylmethyl penicillins, their salts, esters, method of preparation and oral compositions containing them are described. The penicillins give high and prolonged blood levels on oral administration and are active against both Gram-positive and Gram-negative bacteria.

2 Claims, No Drawings

α-AMINOCYCLOALKYLACETAMIDO PENICILLANIC ACIDS AND THEIR SALTS AND ESTERS

This invention relates to penicillin derivatives and is particularly concerned with a new class of penicillins which are derivatives of 6-aminopenicillanic acid and which are of value as antibacterial agents, as nutritional supplements in animal feeds, as agents for the treatment of mastitis in cattle and as therapeutic agents in poultry and animals, including man, in the treatment especially of infectious diseases caused by Gram-positive and Gram-negative bacteria.

6-D-α-aminobenzylpenicillin (or ampicillin) has proved an extremely valuable antibacterial agent, having as it does a relatively broad spectrum of activity against both Gram-positive and Gram-negative bacteria. It is a desideratum to produce a penicillin which is an effective oral drug, and the related penicillin, α-amino-p-hydroxybenzyl-penicillin (or amoxycillin) has an antibacterial spectrum and level of activity similar to ampicillin, but is better absorbed than ampicillin after oral administration to human subjects.

The present invention is based upon the discovery of a class of amino alicyclylmethyl penicillins which, upon oral administration, achieve higher and in some cases more prolonged blood levels than either ampicillin or amoxycillin. In general the new class of penicillins have a high level of activity against both Gram-positive and Gram-negative organisms and thus many of these new compounds may offer therapeutic advantages over ampicillin and amoxycillin.

According to the present invention there is provided a therapeutic composition, suitable for oral administration to animals including man which composition comprises at least one penicillin of general formula (I) or a non-toxic salt or ester thereof:

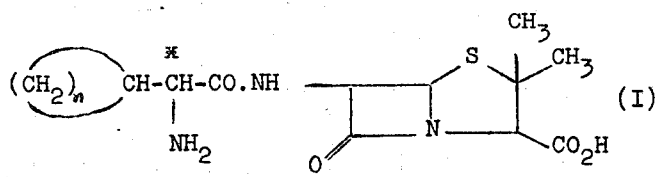

where $n$ is an integer from 2 to 6, together with at least one pharmaceutically acceptable carrier.

The salts are non-toxic salts including non-toxic metallic salts such as sodium, potassium calcium and aluminium, ammonium and substituted ammonium salts, e.g. salts of such non-toxic amines as trialkylamines, including triethylamine, procaine, dibenzylamine, N-benzyl-beta-phenethylamine, 1-ephenamine, N,N'-dibenzylethylenediamine, dehydroabietylamine, N,N'-bis-dehydroabietyethylenediamine and other amines which have been used to form salts with benzylpenicillin and α-aminobenzylpenicillin. The esters of the penicillins defined with reference to formula I are non-toxic esters, particularly those which are readily hydrolysable in the body to give the parent penicillanic acid derivatives. Examples of such esters include acyloxyalkyl esters. particularly acyloxymethyl esters such as the acetoxymethyl and pivaloyloxymethyl esters.

The carbon atom marked by * in formula (I) is an asymmetric carbon atom. Thus, the present invention includes compositions containing the optically active D- and L- enantiomers of the compounds of formula (I) as well as racemates, i.e. the DL- mixtures, compounds or other racemic forms, of such compounds.

Typical oral formulations included within the scope of the present invention will include tablets, pills, capsules, sachets, granules, powders, chewing gum, suspensions, emulsions and solutions; particularly preferred oral formulations are tablets and capsules. Where appropriate and where necessary the formulations may include diluents, binding agents, dispersing agents, surface-active agent, lubricating agents, coating materials, flavouring agents, colouring agents, solvents, thickening agents, suspending agents, sweeteners or any other pharmaceutically acceptable additives, for example, gelatin, lactose, starch, talc, magnesium stearate, hydrogenated oils, polyglycols and syrups. When the formulations are tablets or capsules and the like they will represent pre-measured unit doses but in the case of granules, powders, suspension and the like the formulations may be presented as pre-measured unit doses or in multi-dose containers from which the appropriate unit dose may be withdrawn.

Preferred compounds for incorporation into the compositions of the present invention include the D-, L- and DL- forms of:

6-[α-aminocyclopropylacetamido]penicillanic acid; and

6-[α-aminocyclobutylacetamido]penicillanic acid.

From a second aspect, the present invention provides penicillins of the general formula (II), and non-toxic salts and esters thereof:

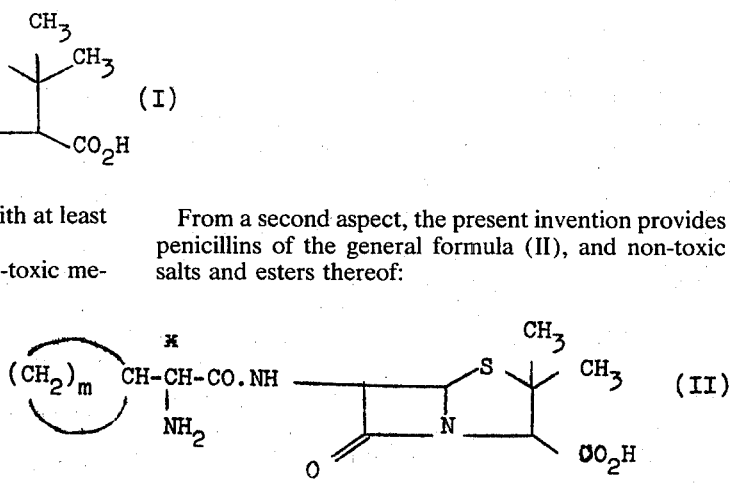

where $m$ is 2,3,4 or 6.

Suitable salts and esters include those which are described with reference to formula (I) above.

Again the penicillins may be in the form of the optically active D- or L- enantiomer or the racemate.

Compounds included within the scope of the present invention include:

6-[DL-α-amino cyclobutyl acetamido]penicillanic acid;

6-[DL-α-amino cyclopentyl acetamido]penicillanic acid;

6-[D-α-amino cyclopentyl acetamido]penicillanic acid;
6-[L-α-amino cyclopentyl acetamido]penicillanic acid;
6-[DL-α-amino cycloheptyl acetamido]penicillanic acid;
6-[DL-α-amino cyclopropyl acetamido]penicillanic acid;
6-[D-α-amino cyclopropyl acetamido]penicillanic acid;
6-[L-α-amino cyclopropyl acetamido]penicillanic acid;
6-[D-α-amino cyclobutyl acetamido]penicillanic acid;
6-[L-α-amino cyclobutyl acetamido]penicillanic acid.

Preferred compounds of the present invention are the D-, L- and DL forms of 6-[α-amino cyclopropyl acetamido] penicillanic acid, and 6-[α-amino cyclobutyl acetamido]penicillanic acid.

The present invention also provides a process for the preparation of penicillins of the formula (II) where $m$ is as hereinbefore described, and non-toxic salts and esters thereof, which process comprises reacting 6-aminopenicillanic acid or a salt or ester thereof or a silyl derivative thereof with a reactive N-acylating derivative of formula (III):

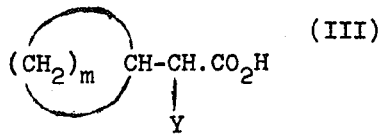

where $m$ is as defined above and Y is an N-protected amino group, and thereafter converting the N-protected group Y to a free amino group, and if a silyl derivative of 6-aminopenicillanic acid was employed, removing the silyl group by alcoholysis or hydrolysis.

By the term "silyl derivative" of 6-aminopenicillanic acid we mean the product of the reaction between 6-aminopenicillanic acid and a silylating agent such as a halotrialkylsilane, a dihalodialkylsilane, a halotrialkoxysilane, a dihalodialkoxysilane or a corresponding aryl or aralkyl silane and compounds such as hexamethyldisilazane. In general halotrialkylsilanes are preferred, especially trimethylchlorosilane. The silylated derivatives of 6-aminopenicillanic acid are extremely sensitive to moisture and hydroxylic compounds, and after reaction with the reactive derivative of compound (III), the silyl group of the intermediate acylated compound can be removed by hydrolysis or alkanolysis.

The reactive derivative of the acid (III) may be an acid halide, e.g. bromide or chloride; the acid azide; the acid anhydride; or a mixed anhydride, e.g. that formed with ethyl chlorocarbonate or ethyl chloroformate.

Alternatively, the acid (III) may be coupled to 6-aminopenicillanic acid by standard coupling reagents, e.g. a carbodiimide, such as dicyclohexylcarbodiimide, or a carbonyldiimidazole.

Examples of suitable N-protected amino groups Y in formula (III) include the protonated amino group (Y = $NH_3^+$) which after coupling reaction reverts to $NH_2$ on simple neutralisation; the benzyloxycarbon amino group (Y = $NH\cdot CO_2\cdot CH_2\cdot Ph$) or substituted benzyloxycarbonylamino groups which are subsequently converted to $NH_2$ by catalytic hydrogenation, and various groups which after coupling regenerate the amino group on mild acid or alkaline hydrolysis.

Examples of N-protected amino groups Y which may subsequently be converted into $NH_2$ by mild acid hydrolysis include enamine groups of general formulas (IV) and (V) or tautomeric modifications thereof:

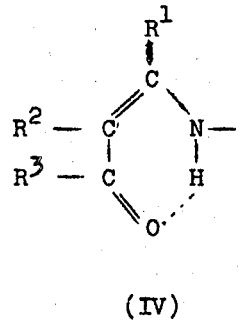 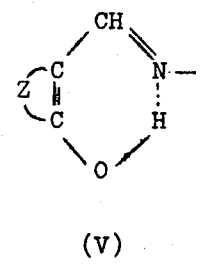

(IV)              (V)

wherein the dotted lines represent hydrogen bonds, $R^1$ is a lower alkyl group, $R^2$ is either H or together with $R^1$ completes a carbocyclic ring. $R^3$ is a lower alkyl or lower alkoxy group and Z represents the residue of a substituted or unsubstituted benzene or napthalene ring.

Examples of the group Y which may subsequently be converted to $NH_2$ by mild alkaline hydrolysis include 2-sulphonyl substituted ethoxycarboxylamino groups $R\cdot SO_2\cdot CH_2\cdot O\cdot CO\cdot NH-$ wherein R represents a substituted alkyl, aralkyl or aryl group.

Another example of a group Y which can be converted into $NH_2$ after coupling of the reactive derivative of the acid (III) with 6-aminopenicillanic acid or a salt or ester thereof is the azido group. In this case the final conversion into $NH_2$ may be brought about either by catalytic hydrogenation or by electrolytic reduction.

The compounds of general formula (III) for use in the present invention may be prepared by known methods. A preferred method of preparation starts from the appropriate cycloalkane aldehyde, which is converted to the acid (III) via a cycloalkyl-5-hydantoin. Another suitable method involves the reaction of the appropriate bromo cycloalkane with diethyl acetamido sodiomalonate.

When an optically active form of a compound of the present invention is to be produced, it is preferable that the reactive derivative of the acid (III) is optically active prior to the reaction with the 6-aminopenicillanic acid, or derivative thereof. Preferably, a resolution step is performed on the lithium salt of the appropriate DL-α-acetamidocycloalkyl acetic acid, and a convenient method is the use of Hog Kidney Acylase I at controlled pH.

The following Examples illustrate the present invention:

EXAMPLE 1

6-[DL-α-amino cyclobutyl acetamido] penicillanic acid

Cyclobutane aldehyde (7.8 g.), ammonium carbonate (46.0 g.) and sodium cyanide (9.6 g.) were suspended in 50% aqueous ethanol (275 ml.). After heating to 50° for 4.5. hours with continuous stirring, the reaction mixture was allowed to stand overnight and then concentrated to about 150 ml. After cooling to 0°, the pH was adjusted to 1.0 with concentrated hydrochloric acid. The product was collected by filtration, dried in vacuo over phosphorus pentoxide to give pale yellow solid, (8.1 g. m.p. 173°). A sample of this material was re-crystallised from water to give pale yellow needles of cyclobutyl-5-hydantoin [m.p. 174°, found C, 48.7; H, 7.0; N, 16.4; $C_7H_{10}N_2O_2$—$H_2O$ requires C, 48.8; H, 7.0; N, 16.3%. $\nu_{max}$ (KBr) 3460 ($H_2O$), 3280 (NH), 1765 and 1705 cm$^{-1}$ (C=O). $\tau[(CD_3)_2SO]$ −0.47 (H, broad, NH), 2.0 (H, broad, NH), 6.03 (H, d. of d. 5 and 1.5 Hz), 6.69 (2H, s, $H_2O$), 8.16 (7H broad, cyclobutyl)].

The hydantoin monohydrate (5.35 g.) and lithium hydroxide (7.31 g.) were suspended in water (110 ml.) and gently refluxed for 25 hours. The solution was concentrated under reduced pressure, acidified to pH 1.0 with concentrated hydrochloric acid, filtered, and the pH readjusted to 5.5 with lithium hydroxide solution. The mixture was evaporated to dryness under reduced pressure and the resultant white solid thoroughly triturated with methanol, (100 ml.), for 1 hour. The fine white solid was collected by filtration, washed with methanol (15 ml.) and dried in vacuo over phosphorus pentoxide to give dl-α-amino cyclobutyl acetic acid, [(3.22 g.), m.p. 278°–282° (d), found C, 55.8; H, 8.95; N, 10.8; $C_6H_{11}NO_2$ requires C, 55.8; H, 8.6; N, 10.8%, $\nu_{max}$ (KBr) 2950, 1650, 1620 and 1570 cm$^{-1}$. $\tau(D_2O + DCl)$ 5.94 (H, d. 8Hz side chain CH), 7.2 (H, broad, ring methine) and 7.94 (6H, broad, cyclobutyl).

DL-α-amino cyclobutyl acetic acid, (1.0 g.), suspended in dry methylene dichloride (25 ml.) was treated at 0° with dry hydrogen chloride gas for 30 minutes. To the resulting suspension was added phosphorous pentachloride (1.7 g.) with stirring for 1.5 hours at 0° to 5° C. Dry acetone (1 ml.) was then added and the mixture evaporated to dryness under reduced pressure. After the addition of dry toluene (3 × 10 ml.) and subsequent re-evaporation under reduced pressure, the residual white solid was triturated with dry diethylether (20 ml.), filtered off in a dry-box and dried in vacuo over phosphorus pentoxide.

A suspension of the acid chloride hydrochloride in dry methylene dichloride (15 ml.) at 5° was added in one portion to a well stirred solution of triethylammonium 6-amino penicillanate (2.45 g.) in dry methylene dichloride (20 ml.) at 0° to 5° C, immediately followed by triethylamine (1.08 ml.). The reaction mixture was stirred for 1 hour at 0° to 5° and the resulting white solid filtered off, washed with dry methylene dichloride (10 ml.) and dry diethyl ether (10 ml.) and finally dried in vacuo over phosphorus pentoxide to yield the required penicillin [(1.65 g.) $\nu_{max}$ (KBr) 1765 cm$^{-1}$ β lactam CO]. This material when subjected to paper chromatography in butanol:ethanol:water had an $R_f$ of 0.25 and was estimated by colorimetric assay with hydroxylamine to be 41% pure.

EXAMPLE 2

6-[DL-α-amino cyclopentyl acetamido] penicillanic acid

DL-α-amino cyclopentyl acetic acid (2.5 g.) was suspended in water (15 ml.) and 1.0N sodium hydroxide solution (17.5 ml.), the resultant solution evaporated to dryness under reduced pressure and desiccated over phosphorus pentoxide for 20 hours. The residue was suspended in dry methanol (30 ml.), methyl acetoacetate (1.79 ml.) added and the mixture stirred and heated under reflux for 45 minutes when most of the methanol was distilled under reduced pressure. Benzene (40 ml.) was then added and the mixture distilled carefully and slowly at atmospheric pressure until the head temperature reached 78°–79°. The remainder of the benzene, approximately 10 ml., was evaporated under reduced pressure and the residue dried over phosphorus pentoxide in vacuo for 20 hours.

The residue was suspended in dry acetone (20 ml.), cooled with stirring to −20° and ethyl chloroformate (1.63 ml.) added followed by one micro-drop of N-methyl morpholine. The mixture was maintained at 0° for 20 minutes, chilled to −40° and to it was added with vigorous stirring a solution of 6-aminopenicillanic acid (3.8 g.) in aqueous acetone (50 ml.) and triethylamine (2.47 ml.). The mixture was stirred for 1 hour further at 0° and then the acetone removed under reduced pressure. The aqueous concentrate was covered with ethyl acetate (60 ml.) and adjusted to pH 1.0 with dilute hydrochloric acid with vigorous stirring for 10 minutes. After separation, the aqueous phase was readjusted to pH 6.0 with triethylamine, evaporated to dryness under reduced pressure and finally dried in vacuo over phosphorus pentoxide for 20 hours. The white residue was thoroughly triturated with dichloromethane (500 ml.), filtered, washed with dry ether and dried in vacuo to give the required penicillin [(6.7 g.) i.r. $\nu_{max}$ (mull) 1780 cm$^{-1}$ β-lactam C=O]. This material when subjected to paper chromatography in butanol:ethanol:water revealed a single zone of antibacterial inhibition at an $R_f$ value of 0.28 and was estimated by colorimetric assay with hydroxylamine to be 50% pure.

EXAMPLE 3

6-[D-α-amino cyclopentyl acetamido] penicillanic acid

D-α-amino cyclopentyl acetic acid (1.43 g.), suspended in dry dichloromethane (20 ml.), was treated at 0° with dry hydrogen chloride gas for 30 minutes. To the resultant suspension was added phosphorus pentachloride (2.2 g.) and dichloromethane (15 ml.) with stirring for 2 hours at 0°. The now homogenous reaction mixture was evaporated to near dryness under reduced pressure, dry diethyl ether (30 ml.) added and the precipitated acid chloride hydrochloride collected in a dry-box, washed with dry diethyl ether and finally dried in vacuo over phosphorus pentoxide for 2 hours.

This solid was suspended in dry dichoromethane (20 ml.) and added rapidly to a solution of triethylammonium 6-amino penicillanate (3.17 g) in dry dichloromethane (20 ml.) at 0° to 5° C, immediately followed by triethylamine (1.4 ml.). The reaction mixture was stirred at this temperature for 1 hour and the resulting solid filtered off, washed with dry dichloromethane, then with diethyl ether and finally dried in vacuo over phosphorus pentoxide to yield the required penicillin, [(2.65 g.) $\nu_{max}$ (nujol) 1770 cm$^{-1}$ β-lactam CO]. The compound, when subjected to paper chromatography in butanol:ethanol:water, revealed a single zone of inhibition at an $R_f$ of 0.37 and was estimated to be 78% pure by colorimetric assay with hydroxylamine.

EXAMPLE 4

6-[L-β-amino cyclopentyl acetamido] penicillanic acid

This penicillin, [(2.3 g.) $\nu_{max}$ (nujol) 1775 cm$^{-1}$ β-lactam CO] was obtained exactly as detailed in Example 3 when L-α-amino cyclopentyl acetic acid (1.43 g.) replaced the D-α-amino acid. The penicillin, $R_f$ 0.3 in butanol:ethanol:water, was estimated by colorimetric assay with hydroxylamine to be 48% pure.

EXAMPLE 5

6-[DL-α-amino cycloheptyl acetamido] penicillanic acid

DL-α-amino cycloheptyl acetic acid was prepared from bromo cyclo heptane and diethyl acetamido sodiomalonate following the experimental procedures of J. T. Hill and F. W. Dunn, J. Org. Chem. 1965, 30 1321 and L. K. Govardham and C. G. Skinner, Biochem. Prepns. 1963, 10, 40. The penicillin [(2.4 g.) $\nu_{max}$ (nujol) 1800 cm$^{-1}$ β-lactam CO], was prepared as described in Example 2. When subjected to paper chromatography in butanol:ethanol:water the penicillin was shown to have an $R_f$ of 0.38 and to be contaminated with some unreacted 6-amino penicillanic acid.

EXAMPLE 6

6-[DL-α-amino cyclopropyl acetamido] penicillanic acid

Cyclopropyl-5-hydantoin (11.9 g.) was prepared exactly as described in Example 1, when cyclobutane aldehyde wad replaced by cyclopropane aldehyde [(7.0 g.), which was synthesised following the methods of H. C. Brown and A. Tsukamoto J. Amer. Chem. Soc., 1961, 83, 4549 and 1964, 86, 1089].

A sample of this material was recrystallised from water to give the pure hydantoin [m.p. 158°–60°, found C, 51.4; H, 5.8; N, 20.0; $C_6H_8N_2O_2$ requires C, 51.4; H, 5.75; N, 20.0% $\nu_{max}$ (KBr) 1750 and 1700 cm$^{-1}$(C=O). τ[(CD$_3$)$_2$SO] −0.42, (H, broad, NH), 2.23 (H, broad, NH), 6.21 (H, d of d, 6 and 1.5 Hz), 9.0 (H, broad, cyclopropyl methine), 9.65 (4H, broad, cyclopropyl)].

DL-α-amino cyclopropyl acetic acid (3.45 g.) was prepared from cyclopropyl-5-hydantoin (4.7 g.) and isolated exactly as detailed in Example 1.

A sample of the fine white solid obtained was recrystallised from water to give crystals of dl-α-amino cyclopropyl acetic acid [m.p. 276°–84° (d), found C, 52.1; H, 7.9; N, 12.3; $C_5H_9NO_2$ requires C, 52.1; H, 7.9; N,12.2% $\nu_{max}$ (KBr) 3000–2700, 1620, and 1580 cm$^{-1}$τ(D$_2$O + DCl), 6.57 (H, d, 9.5Hz, side-chain CH), 8.9 (H, broad, ring methine), and 9.35 (4H, broad, cyclopropyl)].

DL-α-amino cyclopropyl acetic acid (1.5 g.) was suspended in dry methylene dichloride (20 ml.) and treated at 0° with dry hydrogen chloride gas for 50 minutes. To the resulting suspension was added phosphorus pentachloride (8.18 g.) in portions over a period of 31 hours with stirring at 0° to 5°. After a further 1.5 hours dry acetone (2 ml.) was added and the mixture stirred for 35 minutes at room temperature. The suspension was filtered in a dry-box and the fine white solid obtained dried in vacuo over phosphorus pentoxide to yield the acid chloride hydrochloride (1.23 g., $\nu_{max}$ (nujol) 1785 cm$^{-1}$ C=O).

Triethylammonium 6-aminopenicillanate (2.24 g.) was dissolved in dry methylene dichloride (14 ml.), triethylamine (1.07 g.) and N,N-dimethylaniline (1.02 g.) were added and the mixture stirred at room temperature for 2 minutes. The clear solution was then cooled to 5° under a stream of dry nitrogen and trimethylchlorosilane (1.53 g.) was added dropwise. Methylene dichloride (6 ml.) was added and the mixture was refluxed for 1 hour, then cooled to −30° under dry nitrogen and DL-α-aminocyclopropyl acetic acid chloride hydrochloride (1.2 g.) was added portionwise. The reaction mixture was stirred at −10° to −20° for 45 minutes, poured into ice-cold water (30 ml.) and the flask washed out with water (10 ml.). The combined solutions were filtered through a Kieselguhr pad and the pH (2.2 ) of the cooled solution adjusted to 5.5 using triethylamine with vigorous stirring. The methylene dichloride was separated and the aqueous layer was washed with methylene dichloride (3 × 10 ml.) and then evaporated to dryness to give a pale yellow material which was dried in vacuo over fresh phosphorus pentoxide. The dry solid was then stirred with dry methylene dichloride (55 ml.) for 40 minutes and the suspension filtered to a yield a white product which was washed with dry methylene dichloride (2 × 10 ml.) and with dry ether (2 × 10 ml.). The white solid was dried in vacuo overnight over fresh phosphorus pentoxide to give 6[DL-α-amino cyclopropyl acetamido] penicillanic acid [1.58 g., $\nu_{max}$ (KBr) 1765 cm$^{-1}$ β-lactam C=O. τ[(CD$_3$)$_2$SO] 4.53 (2H, broad S, β-lactam protons), 5.92 (H.s, C$_3$ proton), 4.8 (3H, broad, N-H protons), 6.8 (H, broad, side-chain CH), 8.41, 851 (6H, singlets, gem dimethyls), 9.45 (broad, cyclopropyl protons)]

This penicillin when subjected to paper chromatography in butanol:ethanol:water had an $R_f$ value of 0.17 and was estimated to be 68% pure by colorimetric assay with hydroxylamine.

EXAMPLE 7

6-[D-α-amino cyclopropyl acetamido] penicillanic acid

DL-α-acetamidocyclopropyl acetic acid was prepared by a method similar to that of R. H. Wiley and O. H. Borum, J. Amer. Chem. Soc., 1950, 72, 1626.

DL-α-aminocyclopropyl acetic acid (29.4 g.) was added with stirring to a solution of sodium hydroxide (20.9 g.) in distilled water (140 ml.). The solution became homogeneous, was cooled to ca. 5° and acetic anhydride (53 g.) was added dropwise over a period of 1.5. hr. whilst maintaining the temperature below 20°. The pH of the solution was adjusted to 3.0 after stirring for a further 0.75 hr., and was then extracted with chloroform: n-propanol, 3:1 (7×100 ml.) and the combined extracts evaporated down to give a white solid which was dried in vacuo over fresh phosphorus pentoxide. Freeze-drying of the aqueous layer and similar work-up to the above gave further product (total yield 26.0 g., 65%). A sample of the solid was recrystallised from chloroform:n-propanol:ether to give crystals of DL-α-acetamidocyclopropyl acetic acid [m.p 150°–154°, found C, 53.2; H. 7.0; N,8.7; $C_7H_{11}NO_3$ requires C, 53.5; H, 7.0; N, 8.9%. $\nu_{max}$ (KBr) 3340

(NH), 1720 ($CO_2H$) 1600 and 1550 (amide I and II) cm$^{-1}$, $\tau$](CD$_3$)$_2$SO]−0.46 (H, broad, $CO_2H$), 1.87 (H,d, 6.9 Hz., NH), 6.32 (H,t, 8.0 Hz., side-chain CH), 8.18 (3H,s,methyl), 8.95 (H, broad, ring methine), 9.65 (4H, broad, complex, ring methylenes)].

The resolution of DL-α-acetamidocyclopropyl acetic acid was carried out in a similar manner to that used by J. T. Hill and F. W. Dunn, J. Org. Chem., 1965, 30, 1321.

DL-α-acetamidocyclopropyl acetic acid (25.72 g.) was suspended in distilled water (1470 ml.) and the mixture stirred for ca. 10 min. Lithium hydroxide solution (2N, 74 ml.) was then carefully added so as to adjust the pH from ca. 3.0 to exactly 7.6, and the solution stirred for 30 minutes and the pH checked to ensure pH 7.6.

Hog Kidney Acylase I (220 Mg.) was then carefully added and the reaction mixture stirred at room temperature for 3 days. Charcoal was added and the mixture stirred for 20–30 minutes, filtered through Kieselguhr and evaporated to dryness to give a white solid which was dried in vacuo over fresh phosphorus pentoxide. The solid was powdered and methanol (200 ml.) added and the resulting suspension stirred vigorously for ca. 1 hr. The suspension was filtered through a sintered funnel (porosity 3) to give a fine white solid which was dried in vacuo over fresh phosphorus pentoxide to give L(+)-α-aminocyclopropylacetic acid (8.16 g., 87%).

A sample of the solid was recrystallised from water to give crystals of pure L(+)-α-aminocyclopropyl acetice acid [m.p. 276°–86°, $[\alpha]_D^{24}$ + 111.0° (1. in 1N HCl)] having consistent spectroscopic data.

The methanolic solution was evaporated to dryness to give a white solid which was dried in vacuo over fresh phosphorus pentoxide. The solid was then dissolved in water (ca. 100 ml.) with stirring and concentrated hydrochloric acid added to ph 2.5, the solution extracted with chloroform:n-propanol 3:1 (6×100 ml.). The combined extracts were evaporated in vacuo to give a viscous oil which on drying over fresh phosphorus pentoxide in vacuo gave a white solid product (10.84 g., 84%).

A sample was recrystallised from chloroform:n-propanol, 3:1 and ether to give D-α-acetamidocyclopropyl acetic acid [m.p. 128°–31°, $[\alpha]_D^{24}$ −52.5° (1 in EtOH). $\nu_{max}$ (KBr) 3330 (NH), 1710 ($CO_2H$), 1620 and 1540 (amide I and II) cm$^{-1}$, $\tau$[(CD$_3$)$_2$SO] −1.6 (H, very broad, $CO_2H$), 1.86 (H,d,7.0 Hz., NH), 6.33 (H,t,8.0 Hz., side-chain CH),8.16 (3H,s, methyl), 8.95 (H, broad, ring methine),9.65 (4H broad, complex, ring methylenes)].

D-α-acetamidocyclopropylacetic acid (1.0 g.) was dissolved in 6N hydrochloric acid (15.5 ml.) and refluxed. The reaction was followed by removing samples (1.65 ml.) and diluting to 10 ml. and measuring the optical rotation (Na 589 nm) at 20°.

After 80 minutes the optical rotation remained constant and the diluted samples and the remainder of the reaction mixture were combined. D-α-acetamidocyclopropylacetic acid (9.4g.) and concentrated hydrochloric acid (40 ml.) were added and the mixture stirred and refluxed for 2 hrs.

The solution was evaporated to dryness, water (ca. 40 ml.) added, and the solution evaporated to dryness, and the same procedure repeated (to remove hydrochloric acid).

Distilled water (ca. 80 ml.) was added to the solid to give a pale yellow solution which was extracted with ether (100 ml.), treated with charcoal for 5 minutes, and filtered to give a clear colourless solution. Lithium hydroxide solution (4N) was carefully added to the solution to adjust the pH to 5.5, and the mixture evaporated in vacuo to dryness to give a white solid which was dried over fresh phosphorus pentoxide overnight. Methanol (200 ml.) was added to the dry solid and the mixture stirred vigorously for 1 hr., filtered through a sinter (porosity 3) and dried in vacuo over fresh phosphorus pentoxide to give a white solid (6.7 g., 88%).

A sample of the solid was recrystallised from water to give pure D(−)-α-aminocylopropyl acetic acid [m.p. 276°–286°, $[\alpha]_D^{23}$ −109.6° (1 in 1N HCl), found C, 52.2; H, 8.0; N, 12.3; $C_5H_9NO_2$ requires C, 52.1; H, 7.9; N, 12.2%. $\nu_{max}$ (KBr) 3100–2700, 1620 and 1580 cm$^{-1}$, ($D_2O$), 6.88 (H,d, 9.3 Hz., side-chain CH), 8.9 (H, broad, ring methine), and 9.4 (4H, v. broad, ring methylenes)]

D(−)-α-aminocyclopropyl acetic acid (2.0 g.) was dissolved in 5N hydrochloric acid and the solution evaporated in vacuo to give a white solid which was dried in vacuo over fresh phosphorus pentoxide to give D-α-aminocyclopropyl acetic acid hydrochloride (2.57 g., 89%).

D(−)-α-aminocyclopropyl acetic acid hydrochloride (2.57 g.) was suspended in dry methylene dichloride, the mixture cooled 5° and dry hydrogen chloride gas passed in with stirring for ca. 10 minutes. To the resulting suspension was added fresh Analar phosphorus pentachloride (4.79 g.), and the mixture stirred for ca. 0.5–0.75 hrs. Then a further batch of fresh Analar phosphorus pentachloride (0.45 kg., 2.16 mmole) was added and the mixture stirred for a further 25 minutes. Dry Analar acetone (0.3 ml., dried over anhydrous potassium carbonate for a few hours) was added and the mixture stirred for 15 minutes at room temperature. The suspension was then filtered in a dry-box and the fine white solid washed with dry methylene dichloride (10 ml.) and sodium -dried ether (15 ml.) and dried in vacuo over fresh phosphorus pentoxide to yield the D- acid chloride hydrochloride (2.40 g., 81%).

Triethylammonium-6-aminopenicillanate (4.09 g.) was dissolved in dry methylene dichloride (25 ml.), triethylamine (2.7 ml.), and N,N-dimethylaniline (1.96 ml.) were added and the mixture stirred at room temperature for 2 minutes. The clear solution was then cooled to 5° under a stream of dry nitrogen and trimethylchlorosilane (3.3. ml.) was added dropwise. The mixture was stirred for 5 minutes, refluxed in a water-bath at ca. 50° for 1 hr., cooled to −30 to −20° under dry nitrogen and D-α-aminocyclopropylacetyl chloride hydrochloride (2.2 g.) was added portion-wise. The reaction mixture was stirred at −10° to −20° for 30–45 minutes, poured into ice-cold distilled water (30 ml.) and the flask washed out with water (10 ml.). The combined solutions were filtered through a Kieselguhr pad (the filtrate was kept cooled in an ice-bath) and the pH of the cooled solution adjusted to 5.5 by dropwise addition of triethylamine with vigorous stirring.

The methylene dichloride was separated and the aqueous layer washed with methylene dichloride (2×15 ml.). The pale yellow aqueous layer was evaporated in vacuo to lower volume when a white solid began to crystallise out. The solid was filtered off and washed with a small quantity of ice-cold distilled water, dry Analar acetone (10 ml.), sodium-dried ether (10 ml.), dry methylene dichloride (10 ml.) and sodium-dried ether (10 ml.) and dried over fresh phosphorus pentoxide. A further crop was obtained by evaporation of the mother liquor and isolated as above. The white solid isolated was shown to be crystalline analytically-pure 6[D-α-aminocyclopropyl-acetamido] penicillanic acid [1.05 g., 26%, m.p. 212.4° (dec.), $[\alpha]_D^{21} + 239.0°$ (0.5 in $H_2O$), found C, 49.4; H, 6.1; N, 13.3; S, 10.0; $C_{13}H_{19}N_3O_4S$ requires C, 49.8; H, 6.1; N, 13.4; S, 10.2%. $\nu$max (KBr) 3320 (NH) and 1765 d(β-lactam C=O) cm.$^{-1}$, $\tau$($D_2O$/NaHCO$_3$), 4.43 (2H, AB quartet $J_{AB}$ 4.0 hz., β-lactam protons), 5.72 (H,s, $C_3$proton), 6.68 (H,d, 9.0 Hz., side-chain CH), 8.35 (3H,s, CH$_3$ group), 8.47 (3H,s,CH$_3$ group), 9.0 (H, v. broad complex, cyclopropyl methine), 9.4 (4H, broad complex, cyclopropyl methylene)]

This penicillin when subjected to paper chromatography had $R_f$ values of 0.24 (butanol:ethanol:water) and 0.59 (butanol:acetic acid:water) and gave a hydroxylamine colorimetric assay of 100.6%.

EXAMPLE 8

6-[L-α-aminocyclopropylacetamido]penicillanic acid

This was prepared in a similar manner to the D- epimer in Example 7 utilising the L-α-amino-cyclopropylacetyl chloride hydrochloride (1.51 g.) and the disilyl ester of 6-aminopenicillanic acid (prepared in situ).

The fine white solid isolated was shown to be 6[L-α-aminocyclopropylacetamido]penicillanic acid [1.85 g., 76% $\nu_{max}$ (KBr) 3350 (NH) and 1750 (β-lactam C=O) cm.$^{-1}$, $\tau$ [(CD$_3$)$_2$SO], 3.0 (v. broad, N-H protons), 4.53 (2H,s,β-lactam protons), 5.92 (H,s, C$_3$ proton), 6.7 (H, side-chain CH), 8.41 (3H,s,CH$_3$group), 8.52 (3H,s,CH$_3$ group), 9.0 H, v. broad, cyclopropyl methine), and 9.5 (4H,broad, cyclopropyl methylene)]

This penicillin when subjected to paper chromatography had $R_f$ values of 0.16 butanol:ethanol:water) and 0.48 (butanol:acetic acid:water) and gave a hydroxylamine colorimetric assay of 55%.

EXAMPLE 9

6-[D-α-aminocyclobutyl acetamido]penicillanic acid

The synthesis of this penicillin was carried out in a similar manner to that described in Example 7.

DL-α-aminocyclobutyl acetic acid (21.4 g.) was converted to DL-α-acetamidocyclobutyl acetic acid, isolated as a white solid [27.1 g., 95%, m.p. 136°–140°, $\nu_{max}$ 3330 (N-H), $\tau$ (CDCl$_3$) −0.73 (H, broad CO$_2$H), 3.23 (H, d, 7.5 Hz., NH), 5.56 (H,t, 7.5 Hz., side-chain CH), 7.37 (H,broad, complex, ring methine), and 8.05 (9H, broad, complex, ring methylenes and the CH$_3$ group)].

The resolution of DL-α-acetamidocyclobutyl acetic acid (27.1 g.) was carried out on the lithium salt at pH 7.6 at room temperature using Hog Kidney Acylase I for 2 days. The L(+)-α-aminocyclobutyl acetic acid was isolated as a white crystalline solid [8.0 g., 79%, $[\alpha]_D^{22} + 48.3°$ (1 in 1NHCl), found C, 55.7; H, 8.7; N, 10.8; C$_6$H$_{11}$NO$_2$ requires C, 55.8; H, 8.6; N, 10.8%. $\nu_{max}$ (KBr) 3100–2700 and 1620–1540 cm.$^{-1}$, $\tau$ (D$_2$O + DCl), 6.03 (H,d, 8.4 Hz., side-chain CH), 7.25 (H, broad complex, ring methine), and 8.0 (6H, broad complex, ring methylenes)].

The D-α-acetamidocyclobutyl acetic acid was isolated as a white solid [crude yield 99%, m.p. 153°–6°, $[\alpha]_D^{22} -18.0°$ (in EtOH), found C, 55.7; H, 7.9; N, 8.3; C$_8$H$_{13}$NO$_3$ requires C, 56.1; H, 7.7;;N, 8.2% $\nu_{max}$ (KBr) 3330 (NH), 1700, 1620 and 1550 cm.$^{-1}$, $\tau$ [CDCl$_3$ + (CD$_3$)$_2$SO] −0.73 (H,broad, CO$_2$H), 3.12 (H, d, 8.0 Hz., NH), 5.48 (H, t, 8.0 Hz., side-chain CH), 7.28 (H, broad, complex, ring methine) and 8.04 (9H, broad, complex, ring methylenes and CH$_3$ group)].

The D-α-acetamidocyclobutyl acetic acid (12.5 g.) was hydrolysed using 6N hydrochloric acid to give D(−)-α-aminocyclobutyl acetic acid as a white solid (7.7 g., 81%). A sample of this solid was recrystallised from water to give pure D(−)-α-aminocyclobutyl acetic acid as a white crystalline solid [[$\alpha$]$_D^{23}$ −48.5° (1 in 1N HCl), found C, 56.1; H, 8.7; N, 11.0; C$_6$H$_{11}$NO$_2$ requires C, 55.8; H, 8.6; N, 10.8% $\nu_{max}$ (KBr) 3100–2700 and 1620–1540 cm.$^{-1}$, $\tau$ (D$_2$O + DCl) 5.94 (H,d, 8.3 Hz., side-chain CH), 7.2 (H, broad, complex, ring methine) and 7.98 (6H, broad, complex, ring methylenes)].

The D(−) amino acid was converted to D(−)-α-aminocyclobutyl acetyl chloride hydrochloride which was obtained as a white solid (77%,$\nu$(C = O) 1785 cm.$^{-1}$) by reaction of the hydrochloride with phosphorus pentachloride. The D(−)-α-aminocyclobutyl acetyl chloride hydrochloride (2.11 g.) was coupled to the disilyl ester of 6-aminopenicillanic acid (prepared in situ) in a similar manner to that described in Example 7. The penicillin, 6-[D-α-aminocyclobutylacetamido]-penicillanic acid was isolated as a white crystalline solid [1.23 g., 33%, m.p. 208°–10° (dec.), found C,50.9; H, 6.5; N, 12.6; S, 9.9; C$_{14}$H$_{21}$N$_3$O$_4$S requires C, 51.3; H, 6.5; N, 12.8; S, 9.8% $\nu_{max}$ (KBr) 3320 (NH) and 1760 (β-lactam C=O) cm.$^{-1}$, $\tau$ (D$_2$C/NaHCO$_3$), 4.47 (2H,AB quartet J$_{AB}$ 4.0 Hz., β-lactam protons), 5.74 (H,s, C$_3$ proton), 6.0 (H,d, 8.0 Hz., side-chain CH); 7.35 (H, v, broad, ring methine), 8.07 (6H,broad, ring methylenes), 8.37 (3H,s,CH$_3$group), 8.48 (3H, s, CH$_3$ group)].

This penicillin when subjected to paper chromatograhy had $R_f$ values of 0.21 (butanol:ethanol:water) and 0.69 (butanol:acetic acid:water) and gave a hydroxylamine colorimetric assay of 103.8%.

EXAMPLE 10

6-[L-α-aminocyclobutylacetimido]penicillanic acid

This penicillin was prepared in a similar way to the D-epimer in Example 9 utilising L-α-aminocyclobutylacetyl chloride hydrochloride (1.0 g.) and the disilyl ester of 6-aminopenicillanic acid (prepared in situ). The penicillin (1.1.g., $\nu_{max}$ 1770 cm.$^{-1}$ β-lactam C=O] when subjected to paper chromatography had $R_f$ values of 0.20 (butanol: ethanol: water) and 0.59 (butanol:acetic acid: water) and was shown to contain some 6-aminopenicillanic acid.

EXAMPLE 11

The following Table records the blood levels achieved when the compounds listed were given by mouth at 100 mg/kg to squirrel monkeys. The results achieved with ampicillin and amoxycillin are included for comparison purposes.

TABLE $$(CH_2)_n\ CH-CH-CO\cdot NH \begin{array}{c} S \\ \diagup \\ \diagdown \end{array} \begin{array}{c} CH_3 \\ CH_3 \\ \end{array} \quad (I)$$
$$\phantom{(CH_2)_n\ CH}\begin{array}{c}|\\NH_2\end{array}\phantom{CO\cdot NH}O=\!\!\!\diagdown\!\!\!\!N\!\!\!\diagup\!\!\!\!\diagdown CO_2H$$

| Compound | Mean conc$^n$(μg./ml) at hours after dosing | | | | | |
|---|---|---|---|---|---|---|
| | 0.25 | 0.5 | 1.0 | 2.0 | 4.0 | 6.0 |
| 6-D-α-aminobenzyl-penicillin (ampicillin) | — | 6.6 | 12.9 | 5.0 | 1.9 | 0.8 |
| 6-D-α-amino-p-hydroxy-benzylpenicillin (amoxycillin). | — | 17.2 | 15.3 | 5.6 | 1.0 | 0.3 |
| (I), n = 2, D-form | 40.2 | 54.5 | 55.4 | 30.2 | 8.8 | 3.4 |
| (I), n = 2, L-form | 25.0 | 56.3 | 66.8 | 32.0 | 7.5 | 1.5 |
| (I), n = 3, D-form | 7.1 | 8.1 | 5.8 | 2.5 | 0.6 | 0.2 |
| (I), n = 4, D-form | — | 1.9 | 5.4 | 4.6 | 3.1 | 1.5 |
| (I), n = 5, D-form | — | 0.69 | 2.09 | 1.13 | 0.12 | 0.05 |

We claim:

1. A compound which is the D-, L- or DL-form of 6-[α-amino cyclopropyl acetamido] penicillanic acid, or a pharmaceutically acceptable non-toxic salt or carboxylic acid ester thereof which ester is hydrolyzed and converted in vivo to free acid form.

2. An antibacterial pharmaceutical composition for oral administration to human and animals which comprises an antibacterially effective amount of a compound of claim 1 and a pharmaceutically acceptable oral carrier.

* * * * *